United States Patent [19]
Liu

[11] Patent Number: 5,902,293
[45] Date of Patent: May 11, 1999

[54] CAN SUCKER MECHANISM

[75] Inventor: Shih-Ta Liu, Taoyuan, Taiwan

[73] Assignee: Biboting International Co., Ltd., Taoyuan, Taiwan

[21] Appl. No.: 08/892,103

[22] Filed: Jul. 14, 1997

[51] Int. Cl.⁶ ..................................................... A61M 1/00
[52] U.S. Cl. ............................................. 604/313; 604/74
[58] Field of Search ...................................... 604/313–316, 604/36–37, 74–75; 119/14.38–14.43, 14.47–14.53

[56]  References Cited

U.S. PATENT DOCUMENTS 4,740,196  4/1988  Powell ....................................... 604/75

FOREIGN PATENT DOCUMENTS

| 619574 | 4/1927 | France . |
|---|---|---|
| 746185 | 5/1933 | France . |
| 836360 | 1/1939 | France . |
| 956063 | 1/1950 | France . |
| 021797 | 10/1905 | Germany . |
| 122467 | 11/1927 | Switzerland . |
| 124875 | 5/1982 | Switzerland . |

*Primary Examiner*—John G. Weiss
*Assistant Examiner*—David J. Cho
*Attorney, Agent, or Firm*—Smith, Gambrell & Russell, LLP; Beveridge, DeGrandi, Weilacher & Young Intellectual Property Group

[57]  ABSTRACT

A can sucker mechanism includes a can body, a connecting hose and a sucking pump. The can body is fitted with a connecting tube, and in the connecting tube is a check valve. The connecting hose is connected to the connecting tube on the can body, and the sucking pump is connected to the other end of the connecting hose. The sucking pump is used to withdraw air from inside the can body, to produce a negative-pressure status. The can body also is fitted with a vibrator to produce a vibrating and massaging function on the can body, to enhance the curative effects of traditional Chinese can sucking therapy.

4 Claims, 4 Drawing Sheets

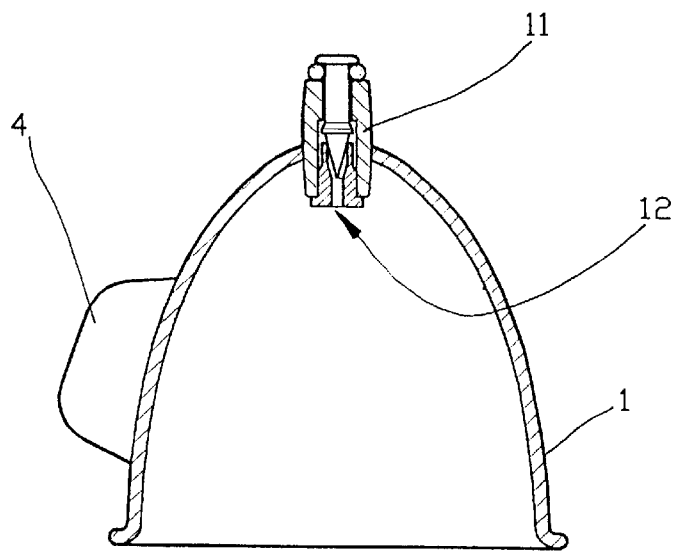
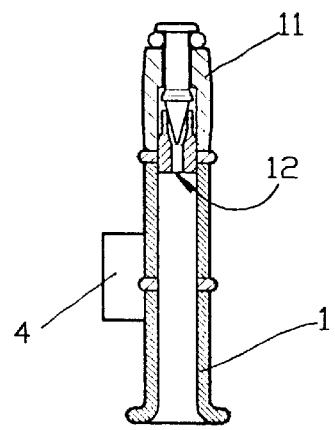
FIG. 3  FIG. 4
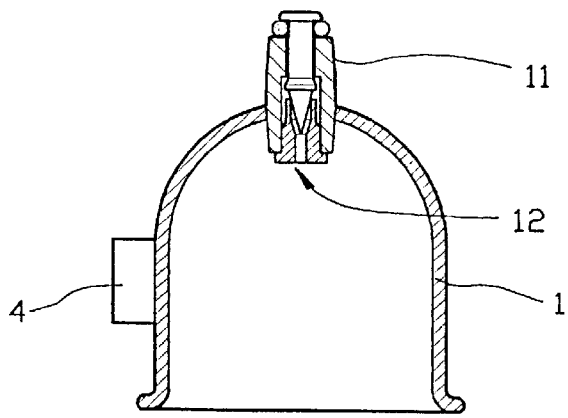
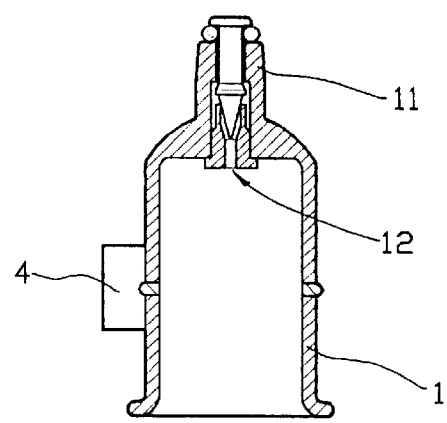
FIG. 5  FIG. 6

CAN SUCKER MECHANISM

BACKGROUND OF THE INVENTION

The subject invention relates to a type of "Can Sucker Mechanism", particularly to a can sucker mechanism that will be applied to the traditional Chinese therapy with a can sucker.

Of some traditional Chinese therapies that have gradually been accepted and affirmed in recent years, the can-sucking therapy has a history of 2000 years in China. Said therapy relates to the burning of moxa punk in a can which is fastened onto the part of a person's body where it needs therapy; first the temperature of the can rises when it is heated, then after a while the temperature of the can drops to form a negative pressure status (semi-vacuum status); since the body part is covered by the can, said part will be filled with blood to improve its blood circulation in said specific part; when it stimulates the "acupuncture point", so called in Chinese traditional therapy, it achieves curative effects. Such a can sucking therapy also is referred to as "vacuum blood purification cure" in Japan, "blood cure" in Russia, or "cup art" in France; therefore, it is widely employed in the whole world.

The regional suction force applied in a can sucking therapy results in passive hyperemia which helps to improve the nutritional conditions and blood circulation of a tissue to stimulate metabolism. Meanwhile, the can sucking process will stimulate nerve systems which reflect their reactions to the cerebral cortex, augment excitement, and contribute to the cure of disorders.

Furthermore, the reason of sore muscles is said to be poor blood circulation due to obstructed capillaries in a muscle tissue, resulting in failure of oxygen supply in the blood. For that reason, the regional congestion in the can sucking therapy will alleviate the soreness.

In older times, the Chinese traditional can sucking therapy employs animal horns to serve as the can bodies, such as cow horns, etc. They were replaced later by bamboo cylinders in the "Shui and Tang" dynasties, then by "ceramic cans or metal cans" in the Ching dynasty. Nowadays, they use acrylic plastic cans for that purpose.

With the changing time, the conventional burning of moxa punk to produce the semi-vacuum status inside the can is now replaced by a manual or electric sucking pump to withdraw air from inside the can, to produce the status of negative pressure. In the modern version, the can is fitted with a hose, the upper part of the hose is fitted with a cone-shaped tube, while inside the hose is fitted with an anti-leak ring, the lower part of said cone-shaped tube pushing against the upper part of the anti-leak ring, the connecting hose is connected to the tube on the can body, said sucking pump is connected to the other end of the connecting hose; To use, the can body is reversed to cover the body part under therapy, so that by pumping the cylinder to suck out air from inside the can body, a negative pressure status will result in the can body, which will cause regional congestion on the part under therapy to achieve curative effects.

However, such therapeutic mechanism is processed under a static circumstance which has a poorer regional congestion effect, so its curative effect will not be satisfactory.

As described above, the Chinese traditional can sucking therapy with manual or electric pumping to withdraw air from the cans to produce a negative pressure status is processed under a static circumstance, so its curative effect by achieving regional congestion is less satisfactory; For that reason, the subject inventor has devoted much time and concentration in the successful design of a can sucking mechanism comprising a can body, a connecting hose and a sucking pump; on the can body is fitted with a connecting hose, inside the connecting hose is fitted with a check valve; said connecting hose is connected to the hose on the can body, the other end of the connecting hose is connected to the pump which withdraws air from inside the can body to cause a negative-pressure status; characterized in that: on the outside of said can body is fitted with a vibrator to create vibrating and massage functions to the can body, thus regional congestion efficiency is enhanced and the curative effect is upgraded.

SUMMARY OF THE INVENTION

The primary objective of the subject invention is to provide a type of traditional can sucking therapy whereby the can body is fitted with a vibrator to enhance regional blood circulation, better stimulation on the acupuncture point, and upgraded curative effects by the can sucking therapy.

To enable better understanding of the subject invention, the following drawings are described in details:

BRIEF DESCRIPTION DRAWINGS

FIG. 3 is the example of embodiment of the subject invention. (1)

FIG. 4 is the example of embodiment of the subject invention. (2)

FIG. 5 is the example of embodiment of the subject invention. (3)

FIG. 6 is the example of embodiment of the subject invention. (4)

Figure 1:
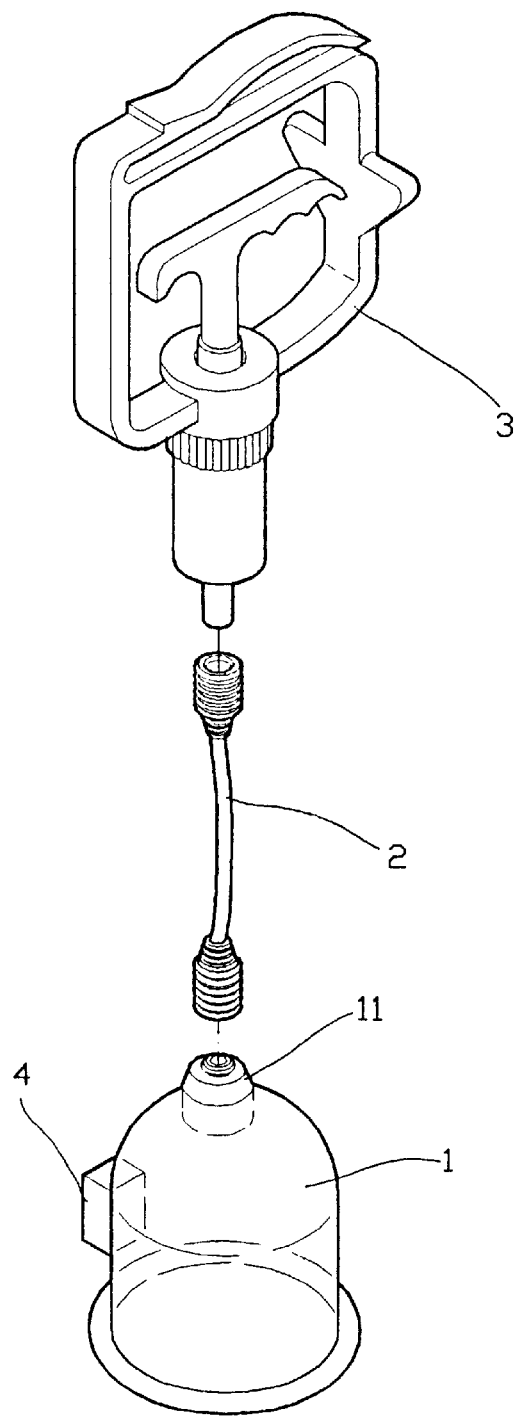
FIG. 1 is the perspective view of the subject invention.

BRIEF DESCRIPTION OF NUMERALS can body 1
connecting tube 11
check valve 12
cup 1'
connecting hose 2
sucking pump 3
vibrator 4

DETAILED DESCRIPTION OF THE INVENTION

Figure 2:
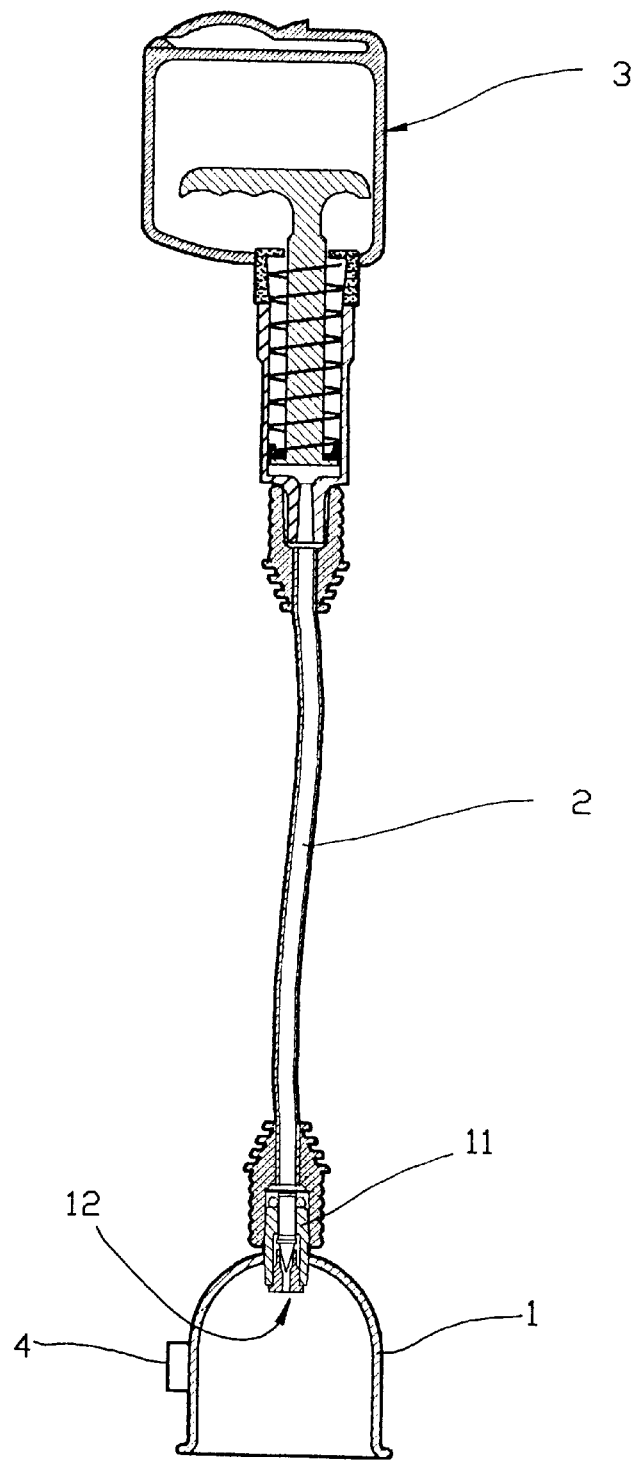
FIG. 2 is the sectional view of the subject invention.

First, referring to FIGS. 1 and 2, the present invention is composed of the can body 1, a connecting hose 2 and a sucking pump 3. The can body 1 is fitted with a connecting tube 11, and the connecting tube 11 is fitted with a check valve 12. The connecting hose 2 is mounted onto the connecting tube 11 of the can body 1, and sucking pump 3 is connected to the other end of the connecting hose 2. The sucking pump will suck out air from the can body 1 to produce a negative-pressure status.

The outside of the can body 1 is installed with a vibrator 4 to produce vibrating and massaging functions on the can body 1.

As configured above, the can body 1 is used to cover the part under therapy, then the sucking pump 3 is activated to withdraw air from inside the can body 1 to create a negative-pressure status (semi-vacuum status) inside the can body 1, and the can body 1 is tightly attached to the skin to have a regional congestion effect. The vibrator 4 is now activated simultaneously to vibrate the can body 1 to have a massaging function; so, regional congestion and massage occur at the same time on the part under therapy to achieve simultaneous effects of blood circulation and stimulation on acupuncture points. The efficiency of traditional can sucking therapy is upgraded.

Referring now to FIGS. 3 to 6, different shapes and forms of the can body 1, including various different diameters and size measurements so that an appropriate can body 1 can be chosen to fit different parts of a human body that needs therapy. Meanwhile, the vibrator 4 will help to upgrade the curative effects of the can sucking therapy.

Furthermore, said vibrator 4 may be a mechanism including an eccentric cam installed on a motor, whereby vibration occurs when the motor is operated; or a coil winding on an iron core to produce the required vibration on the vibrator 4.

And, the vibrator 4 may be fixed onto the can body 1 by way of a band, a fastener, a groove socket, a sucking disc, a magnetic, attachment screws, etc. To suit the circumstances, a fixed installation or a mobile method may be chosen to upgrade its convenience in application.

The power source for said vibrator 4 may be a battery or an outside power connection. To suit the circumstances, different power sources may be selected.

Figure 7:
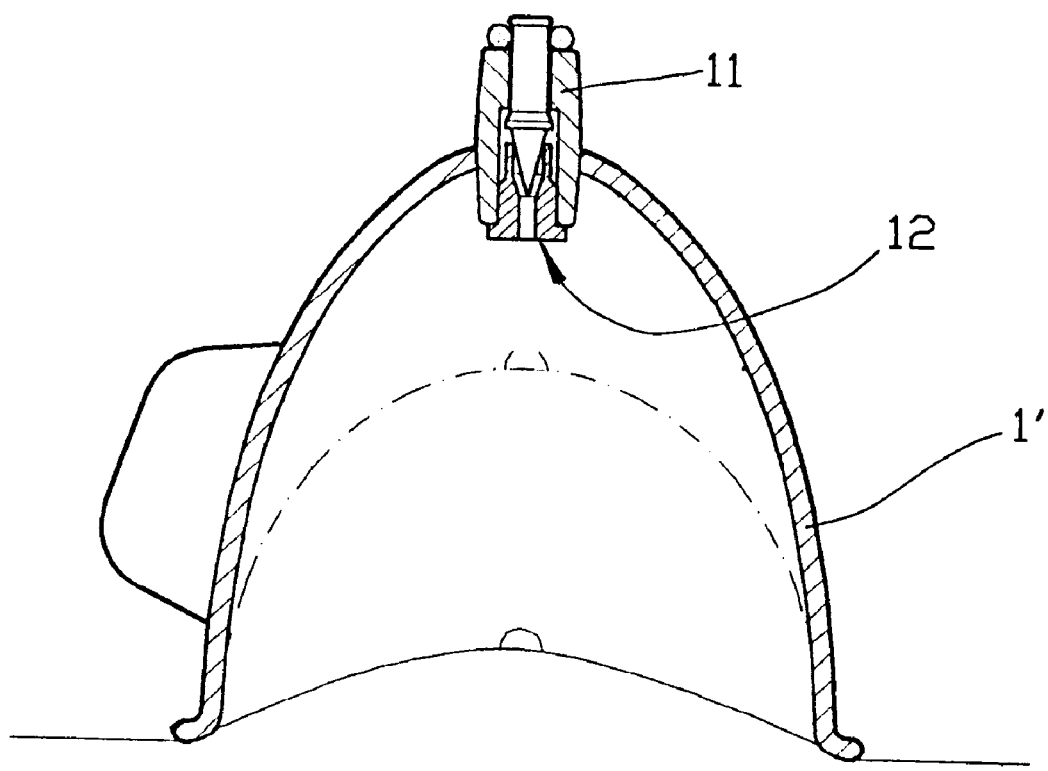
FIG. 7 is the embodied view of the subject invention when applied to a female's breast.

Referring to FIG. 7, the can body 1 may be designed in a cup 1' shaped like a female breast booster to suit the need, On said cup 1' can be the installation of the vibrator 4; the cup 1' is used to cover a female breast, then the sucking pump 3 is used to withdraw air from inside the cup 1', to boost the size of a female breast. Since there is the vibrator 4 installed on the cup 1', it will produce the vibrating and massaging function during the breast boosting process to enhance breast development and breast-beautifying effect.

Summing up, the configuration of the subject invention is unprecedented and with assured above effects, therefore the requirements for a patent are satisfied. Accordingly, this application is duly filed. Your favorable consideration shall be appreciated.

I claim:

1. A mechanism for performing a variation of can sucking therapy, comprising:

a rigid can body having a suction opening and a body engaging opening defined therein;

sucking means engaged in communication with said suction opening for suctioning an interior of said rigid can body to draw a negative pressure state within said interior of said rigid can body when said body engaging opening is sealed against a portion of a body;

vibrating means mounted on said rigid can body for vibrating said rigid can body, and;

an one way check valve arranged in communication with said suction opening and preventing fluid from entering said interior of said rigid can body via said suction opening for maintaining said negative pressure state in said interior of said rigid can body when said body engaging opening is sealed against a portion of a body.

2. A mechanism for performing a variation of can sucking therapy, comprising:

a rigid can body having a suction opening and a body engaging opening defined therein;

sucking means engaged in communication with said suction opening for suctioning an interior of said rigid can body;

vibrating means mounted on said rigid can body for vibrating said rigid can body, and wherein said sucking means draws a negative pressure state within said interior of said rigid can body when said body engaging opening is sealed against a portion of a body;

said sucking means includes a sucking pump, and said sucking means further includes a connecting hose, said connecting hose interposed between said sucking pump and said suction opening defined in said rigid can body and said connecting hose placing said sucking pump in communication with said interior of said rigid can body, and said mechanism further comprising;

an one way check valve arranged in communication with said suction opening and preventing fluid from entering said interior of said rigid can body via said suction opening for maintaining said negative pressure state in said interior of said rigid can body when said body engaging opening is sealed against a portion of a body.

3. The mechanism defined in claim 2, wherein:

said negative pressure state in said interior of said rigid can body is maintained by said one way check valve when said body engaging opening is sealed against a portion of body.

4. The mechanism defined in claim 3 wherein:

said sucking pump comprises a spring actuated hand pump.

* * * * *